United States Patent [19]

Coffman et al.

[11] Patent Number: 5,096,704
[45] Date of Patent: Mar. 17, 1992

[54] METHOD OF TREATING EOSINOPHILIA

[75] Inventors: Robert L. Coffman, Portola Valley; Donna M. Rennick, Los Altos, both of Calif.

[73] Assignee: Schering Corporation, Madison, N.J.

[21] Appl. No.: 556,757

[22] Filed: Jul. 23, 1990

Related U.S. Application Data

[63] Continuation-in-part of Ser. No. 266,909, Nov. 3, 1988, abandoned.

[51] Int. Cl.$^5$ .................. A61K 39/00; C07K 15/28
[52] U.S. Cl. .................. 424/85.8; 530/387.3; 530/388.23; 530/866
[58] Field of Search .............. 424/85.8; 530/387–388

[56] References Cited

U.S. PATENT DOCUMENTS 4,355,023 10/1982 Ehrlich et al. .................. 424/85.8
4,642,334 2/1987 Moore et al. .................. 530/388

OTHER PUBLICATIONS

Skerra et al, Science, vol. 240, pp. 1038–1041 (1988).
Hochman et al, Biochemistry, vol. 12, pp. 1130–1135 (1973).
Exley et al, Lancet, vol. 335, pp. 1275–1277 (1990).
Anasette et al., Transplantation, vol. 50, pp. 49–54 (1990).
Clarkson et al, New England J. Med., vol. 314, pp. 1236–1239 (1986).
Goldstein et al, New England J. Med., vol. 313, pp. 337–342 (1985).
Lowder et al, Cancer Surveys, vol. 4, pp. 359–375 (1985).
Frodin et al, Cancer Research, vol. 50, pp. 4866–4871 (1990).
Lopez, J. Exp. Med. (1/1988) 167: 219–224.
Schumacher, J. Immunology (9/1988) 141: 1576–81.
Sanderson et al., "Molecular and Cellular Biology of Eosinophil Differentiation Factor (Interleukin-5) and Its Effects on Human and Mouse B. Cells", *Imm. Rev.* 102: 29–50, 1988.
Warren et al., "Production of a T-cell Hybrid Producing a Lymphokine Stimulating Eosinophil Differentiation", *Immunology* 54: 615–623, 1985.
Warren et al., "Synergism Among Interleukin 1, Interleukin 3, and Interleukin 5 in the Production of Eosinophils from Primitive Hemopoietic Stem Cells", *J. Immunol.* 140: 94–99, Jan. 1, 1988.

*Primary Examiner*—John Doll
*Assistant Examiner*—Robert D. Budens
*Attorney, Agent, or Firm*—Stephen C. Macevicz

[57] ABSTRACT

A method of preventing eosinophilia associated with certain immune disorders is provided. The method comprises administering an effective amount of an antagonist to human interleukin-5. Preferably, the antagonist is a blocking monoclonal antibody specific for human interleukin-5, or a fragment or binding composition derived therefrom.

4 Claims, 1 Drawing Sheet

METHOD OF TREATING EOSINOPHILIA

This is a continuation-in-part of pending U.S. patent application Ser. No. 07/266,909 filed Nov. 3, 1988, now abandoned.

FIELD OF THE INVENTION

The invention relates generally to a method for treating diseases associated with elevated populations of eosinophils, and more particularly, to a method of inhibiting eosinophil production and accumulation by blocking the stimulatory effects of interleukin-5 (IL-5).

BACKGROUND

Eosinophils are white blood cells of the granulocytic lineage. Their normal function appears to be combating parasitic infections, particularly helminthic infections. However, their accumulation in tissues, a condition referred to as eosinophilia, is also associated with several disease states, most notably asthma, e.g. Frigas et al, J. Allergy and Clinical Immunol., Vol. 77, pgs. 527-537 (1986); Gleich, Hospital Practice (Mar. 15, 1988); and Weller, J. Allergy and Clinical Immunol., Vol. 73, pgs. 1-10 (1984). It is believed that the damage to the epithelial lining of the bronchial passages in severe asthmatic attacks is largely caused by the compounds released by degranulating eosinophils.

Currently glucocorticoid steroids are the most effective drugs for treating the acute effects of allergic diseases, such as asthma. However, prolonged steroid treatment is associated with many deleterious side effects, Goodman and Gillman, The Pharmacological Basis of Therapeutics, 6th Ed. (MacMillan Publishing Company, New York, 1980). Moreover, the steroids apparently do not affect the production or accumulation of granulocytic cells, such as eosinophils, in the afflicted tissues. The availability of alternative or complementary approaches to the treatment of disorders associated with eosinophilia would have important clinical utility.

SUMMARY OF THE INVENTION

The invention is a method of preventing eosinophilia by administering an effective amount of an antagonist to human interleukin-5 (IL-5). Preferably, the antagonists to IL-5 are monoclonal antibodies, or binding compositions derived therefrom by standard techniques.

DETAILED DESCRIPTION OF THE INVENTION

Figure 1:
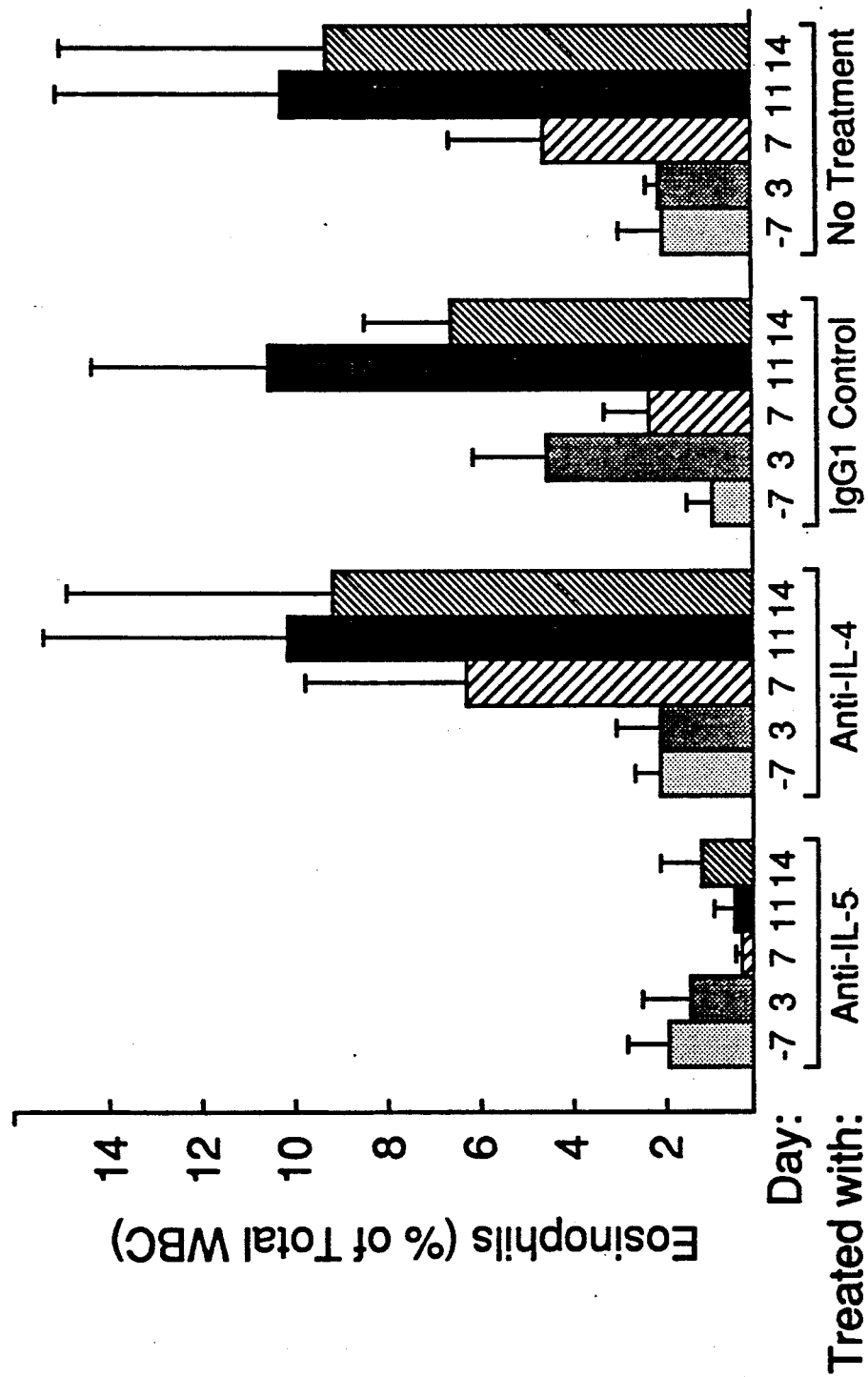
FIG. 1 graphically illustrates data on peripheral blood levels of eosinophils in parasite infected mice with and without treatment with a blocking IL-5 monoclonal antibody.

The invention is based on the discovery that IL-5 increases the production of eosinophils and that antagonists of IL-5 reduce the production of eosinophils and their accumulation in tissues. The method of the invention comprises administering to an individual an effective, or disease-ameliorating amount, of an antagonist to human IL-5. Preferably, antagonists of the invention are derived from antibodies specific for human IL-5. More preferably, the antagonists of the invention comprise fragments or binding compositions specific for IL-5.

Antibodies comprise an assembly of polypeptide chains linked together by disulfide bridges. Two major polypeptide chains, polypeptide chains, referred to as the light chain and the heavy chain, make up all major structural classes (isotypes) of antibody. Both heavy chains and light chains are further divided into subregions referred to as variable regions and constant regions. Heavy chains comprise a single variable region and three different constant regions, and light chains comprise a single variable region (different from those of the heavy chain). The variable regions of the heavy chain and light chain are responsible for the antibody's binding specificity. As used herein, the term "heavy chain variable region" means a polypeptide (1) which is from 110 to 125 amino acids in length, and (2) whose amino acid sequence corresponds to that of a heavy chain of a monoclonal antibody of the invention, starting from the heavy chain's N-terminal amino acid. Likewise, the term "light chain variable region" means a polypeptide (1) which is from 95 to 115 amino acids in length, and (2) whose amino acid sequence corresponds to that of a light chain of a monoclonal antibody of the invention, starting from the light chain's N-terminal amino acid. As used herein the term "monoclonal antibody" refers to homogenous populations of immunoglobulins which are capable of specifically binding to human IL-5. As used herein the term "binding composition" means a composition comprising two polypeptide chains (1) which, when operationally associated, assume a conformation having high binding affinity for human interleukin-5, and (2) which are derived from a hybridoma producing monoclonal antibodies specific for human interleukin-5. The term "operationally associated" is meant to indicate that the two polypeptide chains can be positioned relative to one another for binding by a variety of means, including by association in a native antibody fragment, such as Fab or Fv, or by way of genetically engineered cystiene-containing peptide linkers at the carboxyl termini. Normally, the two polypeptide chains correspond to the light chain variable region and heavy chain variable region of a monoclonal antibody specific for human interleukin-5.

Monoclonal antibodies capable of blocking IL-5 are selected by their ability to inhibit IL-5-induced effects in standard IL-5 bioassays, such as the ability to stimulate the growth and development of eosinophils in in vitro colony forming assays, and the ability to augment in vitro proliferation of the in vivo passaged BCL1 lymphoma cells. The former assays is described is several references, e.g. Todd-Sanford, Clinical Diagnosis by Laboratory Methods, 15th Ed., Davidson and Henry, eds. (1974). The latter assay is described by Hamiblin and O'Garra, pgs. 209-228, in Lymphocytes: A Practical Approach, Klaus ed. (IRL Press, Oxford, 1987). BCL1 cells are available from the ATCC under accession number TIB 197 and are described in Nature, vol. 272, pp. 624-626 (1978); Immunol. Rev, Vol. 48, pgs. 169-195 (1979); and J. Immunol., Vol. 125, pgs. 976-980 (1980). Briefly, the eosinophil assays can be performed as follows using either bone marrow cells or umbilical cord blood cells. Bone marrow cells collected from patients with nonhematologic disease are layered over Ficoll (type 400, Sigma Chemical Co., St. Louis, Mo.), centrifuged (600×g), and the cells at the interface removed. These cells are washed twice in Iscove's Modified Dulbecco's Medium containing 10% fetal calf serum (FCS), resuspended in the same medium and the adherent cells removed by adherence to plastic Petri dishes. The nonadherent cells are added at 105 cells/ml to Iscove's Medium containing 20% FCS, 50 mM 2-mercaptoethanol, 0.9% methylcellulose and varied concentrations of either supernatants known to contain colony stimulating activity or test supernatants. One ml aliquots are plated in 35 mm petri dishes and cultured at 37° C. in a fully humidified atmosphere of 6% $CO_2$ in air. Three days after the initiation of the culture, 1 unit of erythropoietin is added to each plate. Granulocyte-macrophage colonies and erythroid bursts are scored at 10–14 days using an inverted microscope. Cord blood cells collected in heparin are spun at 600×g. The white blood cells at the interface between the plasma and red blood cell peak are transferred to a tube containing 0.17N ammonium chloride and 6% FCS. After 5 min on ice, the suspension is underlaid with 4 ml FCS and centrifuged at 600×g. The cell pellet is washed with Dulbecco's phosphate buffered saline and put through the Ficoll and plastic adherence steps as described above for bone marrow cells. The low density nonadherent cells are collected and placed at 105 cells/culture in the semi-solid culture medium as described above. At the end of the assays, the cellular composition is determined after applying the individual colonies to glass slides and staining with Wright-Geimsa. As mentioned above, eosinophils are determined by staining with Luxol Fast Blue, e.g. Johnson, G. and Metcalf, D., Exp. Hematol., Vol. 8, pgs. 549–561 (1980). Briefly, for the BCL-1-based assay, spleens are removed from the mice (preferably BALB/cByJ or BALB/cdJ) bearing the BCL1 tumor (recoveries vary from $8 \times 10^8$ to $1.3 \times 10^9$ per mouse), a cell suspension is prepared and treated with anti-Thy-1 monoclonal antibodies and complement to deplete T cells (e.g. one spleen in 10 ml of RPMI+5% fetal calf serum, 5 ml of 1:3 guinea pig complement, and 0.5 ml of a pre-titrated anti-Thy-1). Cells in the same medium ($2.5 \times 105$ cells/ml) are plated out into microtiter cultures in 100 ul volumes. The compounds to be tested for IL-5 activity are added to the cultures in 100 ul of medium. The cultures are incubated at 37° C. for 2 days and then assayed for DNA synthesis.

Hybridomas of the invention are produced by well known techniques. Usually, the process involves the fusion of an immortalizing cell line with a B-lymphocyte which produces the desired antibody. Alternatively, non-fusion techniques for generating an immortal antibody producing cell lines are possible, and come within the purview of the present invention, e.g. virally induced transformation: Casali et al., "Human Monoclonals from Antigen-Specific Selection of B Lymphocytes and Transformation by EBV," Science, Vol. 234, pgs. 476–479 (1986). Immortalizing cell lines are usually transformed mammalian cells, particularly myeloma cells of rodent, bovine, and human origin. Most frequently, rat or mouse myeloma cell lines are employed as a matter of convenience and availability; however, because of the lower immunogenicity, human monoclonal antibodies are preferred. Techniques for obtaining the appropriate lymphocytes from mammals injected with the target antigen are well known. Generally, either peripheral blood lymphocytes (PBLs) are used if cells of human origin are desired, or spleen cells or lymph node cells are used if non-human mammalian sources are desired. A host mammal is injected with repeated dosages of the purified antigen, and the mammal is permitted to generate the desired antibody producing cells before these are harvested for fusion with the immortalizing cell line. Techniques for fusion are also well known in the art, and in general, involve mixing the cells with a fusing agent, such as polyethylene glycol. Hybridomas are selected by standard procedures, such as HAT selection. From among these hybridomas, those secreting the desired antibody are selected by assaying their culture medium by standard immunoassays, such as Western blotting, ELISA, RIA, or the like. Antibodies are recovered from the medium using standard protein purification techniques, e.g. Tijssen, Practice and Theory of Enzyme Immunoassays (Elsevier, Amsterdam, 1985). Many references are available for guidance in applying any of the above techniques, e.g. Kohler et al., Hybridoma Techniques (Cold Spring Harbor Laboratory, New York, 1980); Tijssen, Practice and Theory of Enzyme Immunoassays (Elsevier, Amsterdam, 1985); Campbell, Monoclonal Antibody Technology (Elsevier, Amsterdam, 1984); Hurrell, Monoclonal Hybridoma Antibodies: Techniques and Applications (CRC Press, Boca Raton, Fla., 1982); and the like.

Human monoclonal antibodies may be produced using several recently developed techniques, e.g. Pollock et al, pgs. 51–60 in Zola, ed., Laboratory Methods in Immunology, Vol. 1 (CRC Press, Boca Raton, 1989)(in vitro immunization of human spleen cells to produce human monoclonal antibodies); Osband et al, U.S. Pat. No. 4,716,111 (in vitro immunization of human lymphocytes); Winkelhake, U.S. Pat. No. 4,720,459 (human myeloma fusion partner); Kazbor et al, U.S. Pat. No. 4,693,975 (human cell fusion partner for monoclonal antibody production); McCune et al, Science, Vol. 241, pgs. 1632–1639 (1988) and Mosier et al, Nature, Vol. 335, pgs. 257–259 (1988)(immunization and human antibody production in SCID mice transplanted with human fetal tissues); and Kameyama et al, pgs. 173–183 in Zola, ed. (cited above)(production of chimeric human/mouse antibodies in transformed myeloma cells). Accordingly, these references are incorporated by reference.

The use and generation of fragments of antibodies is also well known, e.g. Fab fragments: Tijssen, Practice and Theory of Enzyme Immunoassays (Elsevier, Amsterdam, 1985); and Fv fragments: Hochman et al. Biochemistry, Vol. 12, pgs. 1130–1135 (1973), Sharon et al., Biochemistry, Vol. 15, pgs, 1591–1954 (1976) and Ehrlich et al., U.S. Pat. No. 4,355,023; and antibody half molecules: Auditore-Hargreaves, U.S. Pat. No. 4,470,925. Moreover, such compounds and compositions of the invention can be used to construct bispecific antibodies by known techniques, e.g., via further fusions of hybridomas (i.e. to form so-called quadromas), Reading, U.S. Pat. No. 4,474,493; or via chemical reassociation of half molecules, Brennan et al., Science, Vol. 229, pgs. 81–83 (1985).

Hybridomas and monoclonal antibodies of the invention are produced against either glycosylated or unglycosylated versions of recombinantly produced mature human interleukin-5. Generally, unglycosylated versions of human IL-5 are produced in E. coli, and glycosylated versions are produced in mammalian cell hosts, e.g. CV1 or COS monkey cells, mouse L cells, or the like. Recombinantly produced mature human IL-5 is produced by introducing an expression vector into a host cell using standard protocols, e.g. Maniatis et al., Molecular Cloning: A Laboratory Manual (Cold Spring Harbor Laboratory, New York, 1982); Okayama and Berg, Mol. Cell. Biol., Vol. 2, pgs. 161–170 (1982) and Vol. 3, pgs, 280–289 (1983); Hamer, Genetic Engineering, Vol. 2, pgs. 83–100 (1980) and U.S. Pat. No. 4,599,308; Kaufman et al., Mol. Cell. Biol., Vol. 2 pgs. 1304–1319 (1982); or the like. Construction of bacterial or mammalian expression vectors are well known in the art, once the nucleotide sequence encoding a desired protein is known or otherwise available, e.g. DeBoer in U.S. Pat. No. 4,551,433 discloses promoters for use in bacterial expression vectors; Goeddel et al., in U.S. Pat. No. 4,601,980, and Riggs, in U.S. Pat. No. 4,431,739 disclose the production of mammalian proteins in E. coli expression systems; and Riggs (cited above), Ferretti et al., Proc. Natl. Acad. Sci., Vol. 83, pgs. 599–603 (1986), Sproat et al., Nucleic Acids Research, Vol. 13, pgs. 2959–2977 (1985), and Mullenbach et al., J. Biol. Chem., Vol. 261, pgs. 719–722 (1986) disclose how to construct synthetic genes for expression in bacteria. Accordingly, these references are incorporated by reference. The amino acid sequence of mature human IL-5 is disclosed by Azuma et al, Nucleic Acids Research, Vol. 14, pgs. 9145–9158 (1986), and synthetic genes encoding human IL-5 are available commercially from Beckman Instruments (Fullerton, Calif.)D. Many bacterial expression vectors and hosts are available commercially and through the ATCC.

Antibodies and antibody fragments characteristic of hybridomas of the invention can also be produced by recombinant means by extracting messenger RNA, constructing a cDNA library, and selecting clones which encode segments of the antibody molecule, e.g. Wall et al., Nucleic Acids Research, Vol. 5, pgs. 3113–3128 (1978); Zakut et al., Nucleic Acids Research, Vol. 8, pgs. 3591–3601 (1980); Cabilly et al., Proc. Natl. Acad. Sci., Vol. 81, pgs. 3273–3277 (1984); Boss et al., Nucleic Acids Research, Vol. 12, pgs. 3791–3806 (1984); Amster et al., Nucleic Acids Research, Vol. 8, pgs. 2055–2065 (1980); Moore et al., U.S. Pat. No. 4,642,334; and Skerra et al., Science, Vol. 240, pgs. 1038–1041 (1988). In particular, such techniques can be used to produce interspecific monoclonal antibodies, wherein the binding region of one species is combined with non-binding region of the antibody of another species to reduce immunogenicity, e.g. Liu et al., Proc. Natl. Acad. Sci., Vol. 84, pgs. 3439–3443 (1987).

Antagonists of the invention are administered as a pharmaceutical composition. Such compositions contain a therapeutic amount of at least one of the monoclonal antibodies of the invention, or fragments thereof, in a pharmaceutical carrier. A pharmaceutical carrier can be any compatible, non-toxic substance suitable for delivering the compositions of the invention to a patient. Sterile water, alcohol, fats, waxes, and inert solids may be included in a carrier. Pharmaceutically accepted adjuvants (buffering agents, dispersing agents) may also be incorporated into the pharmaceutical composition. Generally, compositions useful for parenteral administration of such drugs are well known, e.g. Remington's Pharmaceutical Science, 15th Ed. (Mack Publishing Company, Easton, Pa. 1980). Alternatively, compositions of the invention may be introduced into a patient's body by implantable or injectable drug delivery system, e.g., Urquhart et al., Ann. Rev. Pharmacol. Toxicol., Vol. 24, pgs. 199–236 (1984); Lewis, ed. Controlled Release of Pesticides and Pharmaceuticals (Plenum Press, New York, 1981); U.S. Pat. Nos. 3,773,919; 3,270,960; and the like.

When the antagonists of the inventions are derived from antibodies, they are normally administered parenterally, preferably intravenously. Since such protein or peptide antagonists may be immunogenic they are preferably administered slowly, either by a conventional IV administration set or from a subcutaneous depot, e.g. as taught by Tomasi et al, U.S. Pat. No. 4,732,863. When administered parenterally the antibodies or fragments will be formulated in a unit dosage injectable form (solution, suspension, emulsion) in association with a pharmaceutically acceptable parenteral vehicle. Such vehicles are inherently nontoxic and nontherapeutic. Examples of such vehicles are normal saline, Ringer's solution, dextrose solution, and Hank's solution. Nonaqueous vehicles such as fixed oils and ethyl oleate may also be used. A preferred vehicle is 5% dextrose/saline. The vehicle may contain minor amounts of additives such as substances that enhance isotonicity and chemical stability, e.g., buffers and preservatives. The antibody is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml.

Selecting an administration regimen for an antagonist depends on several factors, including the serum turnover rate of the antagonist, the serum level of IL-5 associated with the eosinophilia, the immunogenicity of the antagonist, the accessibility of the target IL-5 (e.g. if non-serum IL-5 is to be blocked), the relative affinity of IL-5 to its receptor(s) versus IL-5 to the antagonist, and the like. Preferably, an administration regimen maximizes the amount of antagonist delivered to the patient consistent with an acceptable level of side effects. Accordingly, the amount of antagonist delivered depends in part on the particular antagonist and the severity of the condition being treated. Guidance in selecting appropriate doses is found in the literature on therapeutic uses of antibodies, e.g. Bach et al., chapter 22, in Ferrone et al., eds., Handbook of Monoclonal Antibodies (Noges Publications, Park Ridge, N.J., 1985); and Russell, pgs. 303–357, and Smith et al., pgs. 365–389, in Haber et al., eds. Antibodies in Human Diagnosis and Therapy (Raven Press, New York, 1977). Preferably, whenever the antagonist comprises monoclonal antobodies or Fab-sized fragments thereof (including binding compositions), the dose is in the range of about 1–20 mg/kg per day. More preferably the dose is in the range of about 1–10 mg/kg per day.

EXAMPLES

The following examples serve to illustrate aspects of the present invention. Selection of vectors, hosts, fusion partners as well as concentration of reagents, temperatures, an the values of other variable parameters are only to exemplify the invention and are not to be considered as limitations thereof.

EXAMPLE I

Production of IL-5-Blocking Monoclonal Antibody TRFK-5

Production of the TRFK-5 hybridoma is described in Schumacher et al, J. Immunol., Vol. 141, pgs. 1576–1581 (1988), which is incorporated by reference. Two 12-week old Lewis rats received three injections each of 0.4 to 1.6 ug of purified mouse IL-5 in Complete Freunds Adjuvant 4 to 5 weeks apart. Both rats were bled at 10 and 18 days after the third injection. The rat demonstrating the higher blocking serum titer received a final i.v. injection of 2 ug of purified mouse IL-5. Three days later, its spleen and popliteal lymph node cells were fused using P3X63Ag8.653 myeloma cells (available from the American Type Culture Collection under accession number CRL 1580) by the method of Kipps and Herzenberg, in Vol.4 Handbook of Experimental Immunology, Weir ed. (Blackwell Scientific Publications, Oxford, 1986). RBC were lysed in distilled water followed immediately by restoration of physiologic osmolarity with HBSS. After fusion using 50% polyethylene glycol (m.w. 1500 to 1800, available from Sigma Chemical Co.), cells were plated at a density of $8.5 \times 10^5$ cells/ml, 100 ul/well, in HAT selection medium. The next day, 150 ul of HAT medium were added to each well, and the medium was refreshed at 5 and 8 days. At 10 days the medium was changed to 100 mM hypoxanthine/16 uM thymidine medium and the cells were maintained in this medium for an additional 14 days. Fourteen days after fusion, hybridoma supernatants were screened by direct blocking of the growth stimulating activity of 0.5 ng/ml of mouse IL-5 in the BCL1 assay. Of 286 wells containing hybridoma growth (43% total wells), four hybridomas producing consistent antibody activity were cloned by limiting dilution in maintenance medium until stable subclones were isolated. IL-5 used as the immunogen was purified from supernatant of the T cell lone MB2-1, described by Giedlin et al, Cell. Immunol., Vol. 97, pg. 357 (1986), by a procedure described in Bond et al, J. Immunol., Vol. 139, pg. 3691 (1987), which references are incorporated by reference. Antibodies produced by TRFK-5 were found to block the biological activities of both mouse IL-5 and human IL-5.

EXAMPLE II

The Effects of Anti-IL-5 Antibody on Parasite-Induced Eosinophilia in Mice

In order to tests the ability of an IL-5 antagonist to reduce the levels of eosinophils in various tissues, 20 Balb/c mice were treated as follows. On day zero all mice were subcutaneously injected with 800 third stage *Nippostrongylus brasiliensis* larvae, e.g. see Ogilvie et al, Experimental Parasitology, Vol. 29, pgs. 138-177 (1971). Five of the mice then injected i.p. (also on day zero) with 2.0 mg of purified monoclonal antibody TRFK-5 in a phosphate buffered solution. Five of the mice were injected i.p. with 2.0 mg of a purified monoclonal antibody that blocks mouse IL-4 as a control. Five of the mice injected i.p. with 2.0 mg of a purified mouse IgG1 as a control. And five of the mice were left untreated as additional controls. On days 3,7,11, and 14 after injection peripheral blood samples were taken from all mice and scored for eosinophils. The results are illustrated in FIG. 1. The peripheral blood of mice treated with the IL-5-blocking antibody shows very clear reductions in eosinophils. After day 14 the mice were sacrificed, their lungs were removed, sectioned, fixed, and stained for eosinophils. A comparison of the numbers of eosinophils in randomly selected microscope fields indicated that in anti- IL-5 treated mice the accumulation of eosinophils in the lung tissues was reduced by about twenty-fold.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Applicants have deposited hybridoma TRFK-5 with the American Type Culture Collection, Rockville, Md., USA (ATCC), under accession number HB9897. This deposit was made under conditions as provided under ATCC's agreement for Culture Deposit for Patent Purposes, which assures that the deposit will be made available to the U.S. Commissioner of Patents and Trademarks pursuant to 35 USC 122 and 37 CFR 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

We claim:

1. A method of treating acute eosinophilia in an individual comprising administering an effective amount of an antagonist to human interleukin-5, wherein said antagonist to human interleukin-5 is selected from the group consisting of a non-human monoclonal antibody capable of blocking the biological activity of human interleukin-5, a fragment of a non-human monoclonal antibody capable of blocking the biological activity of human interleukin-5, and a binding composition comprising the heavy chain variable region and light chain variable region of a non-human monoclonal antibody capable of blocking the biological activity of human interleukin-5.

2. The method of claim 1 wherein said fragment of said monoclonal antibody is an Fab fragment.

3. The method of claim 1 wherein said step of administering further includes intravenous delivery of an amount of said antagonist in the range of about 1-20 mg/kg body weight of said individual per day.

4. The method of claim 1 wherein said monoclonal antibody is a chimeric antibody consisting of human constant regions and non-human variable regions.

* * * * *